United States Patent
Aasberg-Petersen et al.

(10) Patent No.: US 9,162,886 B2
(45) Date of Patent: Oct. 20, 2015

(54) PROCESS FOR REFORMING HYDROCARBONS

(75) Inventors: Kim Aasberg-Petersen, Allerød (DK); Peter Seier Christensen, Virum (DK); Thomas Sandahl Christensen, Lyngby (DK)

(73) Assignee: Haldor Topsøe A/S, Lyngby (DK)

( * ) Notice: Subject to any disclaimer, the term of this patent is extended or adjusted under 35 U.S.C. 154(b) by 0 days.

(21) Appl. No.: 14/129,244

(22) PCT Filed: Jun. 20, 2012

(86) PCT No.: PCT/EP2012/061809
§ 371 (c)(1),
(2), (4) Date: Jan. 31, 2014

(87) PCT Pub. No.: WO2013/000782
PCT Pub. Date: Jan. 3, 2013

(65) Prior Publication Data
US 2014/0135409 A1    May 15, 2014

(30) Foreign Application Priority Data

Jun. 29, 2011 (DK) ................................. 2011 00485
Nov. 16, 2011 (EP) ..................................... 11009101
Dec. 6, 2011 (DK) ................................. 2011 00947

(51) Int. Cl.
*C01B 3/24* (2006.01)
*C01B 3/38* (2006.01)
(Continued)

(52) U.S. Cl.
CPC ... *C01B 3/24* (2013.01); *C01B 3/38* (2013.01); *C01B 3/382* (2013.01); *C07C 1/0485* (2013.01);
(Continued)

(58) Field of Classification Search
CPC ............... C01B 2203/0227; C01B 2203/0233; C01B 2203/0255; C01B 2203/0261; C01B 2203/062; C01B 2203/1235; C01B 2203/1258; C01B 2203/1276; C01B 2203/142; C01B 2203/143; C01B 2203/148; C01B 3/38; C01B 3/382; C01B 3/24; C07C 1/0485; C10G 2/32
USPC ............. 252/373; 422/9, 245.1; 518/702, 703
See application file for complete search history.

(56) References Cited

U.S. PATENT DOCUMENTS

| 5,763,716 A | 6/1998 | Benham et al. |
| 2002/0120018 A1 | 8/2002 | Moore |

(Continued)

FOREIGN PATENT DOCUMENTS

| EP | 0 989 093 A2 | 3/2000 |
| EP | 1 860 063 A1 | 11/2007 |

(Continued)

OTHER PUBLICATIONS

A. Al-Meshari et al., "Metal Dusting Behaviour of Furnace Tube Alloys." ARPN Journal of Engineering and Applied Sciences, vol. 4, No. 8, pp. 68-81, Oct. 2009.

(Continued)

*Primary Examiner* — Jafar Parsa
*Assistant Examiner* — Amy C Bonaparte
(74) *Attorney, Agent, or Firm* — Dickstein Shapiro LLP (57) ABSTRACT

The invention relates to a process for the production of synthesis gas by the use of autothermal reforming in which tail gas from downstream Fischer-Tropsch synthesis is hydrogenated and then added to the autothermal reforming stage.

14 Claims, 3 Drawing Sheets

(51) Int. Cl.
*C07C 1/04* (2006.01)
*C10G 2/00* (2006.01)
*C10K 3/02* (2006.01)

(52) U.S. Cl.
CPC ... *C10G 2/32* (2013.01); *C10K 3/02* (2013.01); *C01B 2203/0227* (2013.01); *C01B 2203/0233* (2013.01); *C01B 2203/0255* (2013.01); *C01B 2203/0261* (2013.01); *C01B 2203/062* (2013.01); *C01B 2203/1235* (2013.01); *C01B 2203/1258* (2013.01); *C01B 2203/1276* (2013.01); *C01B 2203/142* (2013.01); *C01B 2203/143* (2013.01); *C01B 2203/148* (2013.01)

(56) References Cited

U.S. PATENT DOCUMENTS

| | | | |
|---|---|---|---|
| 2002/0143219 A1* | 10/2002 | Price et al. | 585/16 |
| 2003/0134911 A1* | 7/2003 | Schanke et al. | 518/703 |
| 2004/0063797 A1 | 4/2004 | Aasberg-Petersen et al. | |
| 2008/0234397 A1* | 9/2008 | Gimpel et al. | 518/700 |
| 2009/0184293 A1 | 7/2009 | Han | |
| 2009/0186952 A1 | 7/2009 | Steynberg et al. | |

FOREIGN PATENT DOCUMENTS

| | | |
|---|---|---|
| WO | WO 01/42175 A1 | 6/2001 |
| WO | WO 01/98239 A1 | 12/2001 |
| WO | WO 03/035590 A1 | 5/2003 |
| WO | WO 2006/056594 A1 | 6/2006 |
| WO | WO 2007/069197 A2 | 6/2007 |

OTHER PUBLICATIONS

D. J. Young et al., "Recent Advances in Understanding Metal Dusting: A Review." Materials and Corrosion, vol. 62, No. 1, pp. 7-28, 2011.

* cited by examiner

PROCESS FOR REFORMING HYDROCARBONS

FIELD OF THE INVENTION

The present invention relates to a process for the production of synthesis gas used for the production of hydrocarbons by Fischer-Tropsch synthesis. The invention relates in particular to a process for the production of synthesis gas by the use of autothermal reforming in which tail gas from a downstream process, in particular Fischer-Tropsh synthesis, is hydrogenated and then added to the autothermal reforming. In a more general aspect the invention encompasses the removal of olefins in a gas to reduce metal dusting of metal parts in contact with the gas, particularly for the reduction of metal dusting in ATR, CPO or POx and other downstream equipment through which the gas is passed.

BACKGROUND OF THE INVENTION

The production of synthesis gas for Fischer-Tropsch synthesis is typically obtained by passing a hydrocarbon feed through primary and secondary reforming stages. The primary reforming is often conducted in tubular steam reformers or heat exchange reformers, while the secondary reforming is typically conducted in autothermal reformers. When combining a heat exchange reformer with a subsequent autothermal reformer, the hot effluent gas from the autothermal reformed is usually used as heating medium in the heat exchange reformer. It is known to recycle tail gas from Fischer-Tropsch synthesis as part of the hydrocarbon feed used to produce the synthesis gas in the primary and secondary reforming stages. Tail gas can be added prior to the primary reforming or to the primary reformed gas before entering the secondary reforming (typically autothermal reforming).

Tail gas from Fischer-Tropsch synthesis contains hydrogen, carbon monoxide, carbon dioxide as well as light hydrocarbons in the form of paraffins such as methane, ethane, propane and not least olefins such as propylene. The tail gas may also include alcohols and other higher hydrocarbons of both paraffinic and olefinic nature. It is known that the addition of such tail gas to the synthesis gas production section enables that there is sufficient carbon dioxide during the reforming to achieve the desired $H_2/CO$ molar ratio, typically about 2.0.

As used herein "tail gas" means off-gas from the Fischer-Tropsch synthesis stage which is not re-used in said stage.

Hydrogenation of tail gas is known in the art. For instance, in GB 632386 tail gas from Fischer-Tropsch synthesis is hydrogenated in order to increase the otherwise low heating value of this gas caused by the presence of i.a. carbon dioxide, carbon monoxide and hydrogen.

WO-A-0142175 discloses a process in which tail gas is hydrogenated in order to saturate any unsaturated hydrocarbons and is then reformed in a separate steam reformer. The hydrogenation serves to decrease the tendency towards coking in the subsequent high temperature treatment of the steam reformer, since the tendency to coking in said reformer is greater when unsaturated hydrocarbons are present in the tail gas. The resulting reformed tail gas may subsequently also be passed to an autothermal reformer. Accordingly, a steam reformer is used between the hydrogenation stage and the autothermal reformer.

EP-A-1860063 discloses a process in which off-gas from Fischer-Tropsch synthesis where olefins present in the off-gas are first hydrogenated and then converted to hydrogen by a reforming process. Olefins are hydrogenated because of carbon deposition or coking of catalysts used in the hydrogen manufacturing unit and which form hot spots on the catalyst and the reformer reactor tubes. Thus, olefins are removed to avoid coking in a steam reformer having reformer tubes such as a fired reformer.

SUMMARY OF THE INVENTION

We have now found out that the addition of tail gas to the autothermal reformer (ATR), or catalytic partial oxidation reactor (CPO), or non-catalytic partial oxidation reactor (POx), which is desirable in order to adjust the $H_2/CO$ ratio in the synthesis gas, has the severe drawback of promoting metal dusting corrosion, particularly in the burner parts of the ATR or CPO, yet by hydrogenation of the tail gas prior to its direct addition to the ATR such metal dusting is significantly reduced. It has come as a surprise to the applicant that the removal of particularly olefins in the tail gas via hydrogenation conveys the critical advantage of significantly reducing the aggressiveness of the tail gas and hence reducing or eliminating metal dusting in the ATR, or CPO or POx. At the same time the benefits of using tail gas to adjust the $H_2/CO$ ratio are maintained.

The reduction or elimination of metal dusting in an apparatus, e.g. ATR, CPO or POx, according to the simple, economical and elegant solution provided by the present invention translates directly into the reduction or elimination of costly down-time periods in the plant and reduces thereby maintenance costs. Metal dusting has otherwise been mitigated through the use of resistant alloy compositions or metallic coatings that form protective surfaces under metal dusting conditions, and/or by operating the reformer at less metal dusting aggressive conditions but which on the other hand impair the process. Yet even the use of expensive and otherwise effective alloys against metal dusting such as Inconel 690 cannot withstand metal dusting attack when exposed to tail gas from Fischer-Tropsch synthesis.

Metal dusting is a type of metallic corrosion that may be encountered when gases containing carbon monoxide come into contact with metals above ca. 400° C., particularly in the range 400-800° C. Metal dusting conveys the disintegration of metals to dust and is described extensively in the literature.

Metal dusting is a highly complex corrosion process which is not completely understood. However, it is often represented by the following reaction:

$$CO + H_2 \rightarrow C + H_2O \qquad (1)$$

The formed carbon results in corrosion of the construction material possibly by a mechanism including carbide formation and/or dissolution of the carbon in the metal material.

Carbon formation via the exothermic reactions $2CO \rightarrow C + CO_2$ (Boudouard reaction) and $CO + H_2 \rightarrow C + H_2O$ (CO—reduction) is a precursor for metal dusting (MD) corrosion. The exothermic reactions are favoured at low temperatures. However, the reaction rates are higher at higher temperatures. As a result, the MD potential for a given gas will be highest in a medium temperature range, typically in the range of about 400-800° C.

It has to be appreciated, however, that metal dusting and coking are two different phenomena. While metal dusting refers to catastrophic corrosion of metal parts, coking is associated with the catalyst. Coking refers more specifically to carbon formation negatively affecting the catalyst of a steam reformer such as a tubular reformer due to formation of carbonaceous elements that deposit and dissociate on the nickel surface or support material of the steam reforming catalyst (typically a nickel-based catalyst). This may convey also the development of hot spots in the tubes containing the catalyst. Accordingly, for the skilled person metal dusting and coking are two different phenomena: while it has been known for long that the presence of olefins causes coke deposition in catalyst beds, no one has ever seen nor expected that olefins are also responsible for causing such a different phenomenon as metal dusting.

Accordingly, in a first aspect of the invention we provide a process for the production of synthesis gas from a hydrocarbon feedstock with reduced metal dusting potential in at least the burner parts of an autothermal reformer (ATR), catalytic partial oxidation reactor (CPO), or partial oxidation reactor (POx) comprising: passing said hydrocarbon feedstock through an ATR, CPO or POx, and withdrawing a stream of hot effluent synthesis gas from the ATR, CPO or POx, passing tail gas from a Fischer-Tropsch synthesis stage through a hydrogenation stage to produce a hydrogenated tail gas and adding the hydrogenated tail gas directly to said ATR, CPO or POx.

The hydrogenation of the tail gas results in a gas that protects the ATR, CPO or POx from metal dusting, particularly for ATR and CPO the burner metal parts located at the inlet of the reactor and thus upstream the catalyst bed, as it unexpectedly turns out that the absence of olefins makes a gas less aggressive with respect to metal dusting corrosion.

Hence, there is provided in an elegant and simple manner a solution to the long-standing problem of metal dusting of metal parts in the ATR, CPO or POx, particularly burner parts of the ATR, which were encountered when incorporating tail gas from Fischer-Tropsch synthesis into the process.

As used herein the term "reduced metal dusting potential in at least the burner parts of an autothermal reformer (ATR), catalytic partial oxidation reactor (CPO), or partial oxidation reactor (POx)" means that the metal dusting potential is reduced in any metal part within the reactor being in contact with the process gas fed to the it (ATR, CPO, POx) including burner metal parts, particularly for ATR or POx. It would be understood by the skilled person that ATR and POx imply the use of a burner at the top of the reactor. ATR and CPO use a catalyst bed below the combustion zone. CPO means a catalytic reactor or catalytic gasifier which does not always require the use of a burner, but a mixer instead. Further, in a POx (gasifier) there is no use of catalyst. The term ATR includes secondary reformers.

Since the tail gas contains carbon monoxide, carbon dioxide, hydrogen, various hydrocarbons including olefins and a range of other components as described above, the gas is converted by reducing the olefin concentration by hydrogenation according to the following reaction $C_3H_6 + H_2 \leftrightarrow C_3H_8$. The reaction is given for propylene hydrogenation but hydrogenation of other olefins takes place according to a similar reaction.

Catalysts suitable for selectively hydrogenating the olefins to saturated hydrocarbons are preferably based on copper, for instance a Cu/ZnO catalyst, or a combination of copper and a noble metal, for instance platinum or palladium. A copper based catalyst, such as Cu/ZnOhu0 catalyst, is particularly active in the selective hydrogenation of olefins to paraffins with reduced formation or without the formation of methanol or higher alcohols having two or more carbon atoms in their structure.

In connection with the above and below embodiments, the hydrogenation is preferably conducted in a cooled reactor, particularly at a temperature in the range 100-150° C. or higher, for instance 185° C. This enables high conversion of olefins such as $C_3H_6$ and $C_4H_8$ while at the same time avoiding significant formation of methanol or higher alcohols and other by-products. Alternatively, the hydrogenation is conducted in an adiabatic reactor in which the inlet temperature is preferably in the range 70-120° C., more preferably 80-100° C., and the outlet temperature is 120-210° C., preferably 140-190° C., more preferably 150-185° C.

The pressure in the hydrogenation step is in the range 20-70 bar, preferably 20-50 bar, more preferably 20-40 bar.

In one embodiment of the invention said hydrocarbon feedstock is a gas that has passed through at least one adiabatic pre-reforming stage.

Adiabatic pre-reforming is preferably conducted in a fixed bed reactor containing a reforming catalyst, thereby converting all higher hydrocarbons into a mixture of carbon oxides, hydrogen and methane. This endothermic process is accompanied by the equilibration of exothermic methanation and shift reactions. Removal of higher hydrocarbons allows a higher preheat temperature to the subsequent steam reforming.

In another embodiment of the invention said hydrocarbon feedstock is a gas that has passed through at least one steam reforming stage. The steam reforming stage may for instance be tubular reforming (steam methane reforming, SMR) or heat exchange reforming (convective reforming).

In yet another embodiment, the invention encompasses also a process wherein said hydrocarbon feedstock is a gas mixture resulting from dividing a raw hydrocarbon feed gas into two streams, passing the first stream through at least one steam reforming stage to form a primary reformed gas, using the second stream as a by-pass stream to said steam reforming stage, and subsequently combining said primary reformed gas with the by-pass stream to form said hydrocarbon feedstock.

According to this embodiment, steam reforming is arranged in series with the ATR, CPO or POx.

In a separate embodiment, an arrangement where steam reforming is arranged in parallel with the ATR, CPO or POx, is also provided. Hence, the process comprises dividing a raw hydrocarbon feed gas into two streams, by which one of the streams formed becomes said hydrocarbon feedstock, and passing the other stream through at least one steam reforming stage to form a reformed gas.

In another embodiment in combination with anyone of the above or below embodiments, there is provided a process wherein the steam reforming stage is heat exchange reforming, and where at least a portion of the hot effluent synthesis gas from the ATR, or CPO, or POx stage is used as heating medium in said heat exchange reforming.

Hence, one preferred embodiment is a process in which a heat exchange reformer is arranged upstream and in series with an ATR or CPO, preferably an ATR. The raw hydrocarbon feed, for example desulphurised natural gas, is mixed with steam and the resultant mixture is directed to the catalyst side of the heat exchange reformer. In the heat exchange reformer, the gas is then steam reformed according to the reactions: $CH_4 + H_2O \leftrightarrow CO + 3H_2$ and $CO + H_2O \leftrightarrow CO_2 + H_2$. The gas leaving the heat exchange reformer is close to chemical equilibrium for the reactions above. Typically, the exit temperature is 600-850° C. or preferably 675-775° C. The primary reformed gas leaving the heat exchange reformer is passed to the ATR or CPO. In the reactor (ATR or CPO) also oxygen and in some cases a small amount of steam is added. Synthesis gas is formed by a combination of steam reforming and partial oxidation in the reactor. The gas leaving the reactor is free of oxygen and generally the above reactions are close to chemical equilibrium. The temperature of this hot effluent gas from e.g. an autothermal reformer is between 950 and 1100° C., typically between 1000 and 1075° C.

This hot effluent gas leaving the reactor comprises carbon monoxide, hydrogen, carbon dioxide, steam, residual methane, and various other components including nitrogen and argon. This synthesis gas is passed to the non-catalytic side of the heat exchange reformer, where it is cooled by supplying heat to the catalytic side of the heat exchange reformer by indirect heat exchange. The exit temperature from this side of the heat exchange reformer would typically be in the range from 500-800° C.

It also follows that in another preferred embodiment a heat exchange reformer is arranged in parallel with an ATR, CPO or POx, preferably an ATR, and hot effluent synthesis gas from the ATR, CPO or POx is used to provide heat for the endothermic reforming reactions in the heat exchange reformer.

In the parallel arrangement said hot effluent synthesis gas is combined with said reformed gas before, during or after said hot effluent synthesis gas has delivered heat to the heat exchange reforming. Preferably, said hot effluent synthesis gas is combined with said reformed gas before it has delivered heat to the heat exchange reforming.

In yet another embodiment in combination with one of the above or below embodiments, the process comprises also adding a stream comprising steam to said hot effluent synthesis gas, said reformed gas, or the combined stream of hot effluent synthesis gas and reformed gas.

Hence, regardless of whether the heat exchange reformer is arranged in series or in parallel with the ATR, CPO or POx, steam is introduced to the gas from the ATR, CPO or POx delivering heat to the heat exchange reformer. This enables reduction of metal dusting in the metal parts, particularly the shell side, of the heat exchange reformer, particularly where the heat exchange reformer is in series arrangement with the ATR, CPO or POx. This stream comprising steam contains preferably more than 90 vol % of steam ($H_2O$ in the vapour phase), more preferably more than 95%, and most preferably more than 99%. Preferably, the temperature of the hot effluent synthesis gas is 950 to 1050° C., more preferably 1025° C., while the steam added is preferably at 271° C. at 55 barg, thus resulting in a temperature of the mixed stream, i.e. hot effluent synthesis gas combined with stream comprising steam, of 900 to 990° C.

In a further embodiment in combination with anyone of the above or below embodiments, the at least one adiabatic pre-reforming stage is conducted prior to dividing said raw hydrocarbon feed. Hence, prior to dividing the raw hydrocarbon feed gas in separate streams in the series or parallel arrangements, adiabatic pre-reforming of the raw hydrocarbon feed (typically comprising methane and higher hydrocarbons) is conducted.

In an another embodiment in combination with anyone of the above or below embodiments, the process comprises also mixing the hydrogenated tail gas with the hydrocarbon feedstock prior to conducting reforming in the ATR, CPO or POx; or alternatively, adding the hydrogenated tail gas to the ATR, CPO or POx as a separate stream.

In connection with the operation of the series arrangement as described above, there is also provided a process comprising mixing the hydrogenated tail gas with said by-pass stream prior to conducting reforming in the ATR, CPO or POx; or alternatively, mixing the hydrogenated tail gas with said primary reformed gas.

In yet a further embodiment in combination with anyone of the above embodiments, the process further comprises of converting the synthesis gas into liquid hydrocarbons, particularly diesel via Fischer-Tropsch synthesis.

In a second aspect the invention encompasses the use of hydrogenated tail gas from a Fischer-Tropsch synthesis stage as means for reduction of metal dusting in an autothermal reformer (ATR), catalytic partial oxidation reactor(CPO), or partial oxidation reactor (POx).

Hence, according to this aspect the invention encompasses the use of a known substance (hydrogenated tail gas) to obtain the surprising technical effect of reduced metal dusting in an ATR, CPO or POx. Alternative expensive methods such as the provision of resistant alloy compositions or metallic coatings that form protective surfaces under metal dusting conditions are thus avoided.

Tail gas from Fischer-Tropsch synthesis is hydrogenated, thereby converting olefins (alkenes) into alkanes, and thus unexpectedly results in reduction of metal dusting in at least the burner parts of the reactor compared to a situation where the tail gas is added directly, without being hydrogenated. Since the use of tail gas is desirable in order to adjust the $H_2/CO$ ratio in the synthesis gas, this is now possible without risking expensive downtime periods and maintenance costs in the ATR, CPO or POx due to metal dusting issues.

The hydrogenated tail gas contains preferably less than 1 mol % olefins, more preferably less than 1 mol %, most preferably below 0.5 mol %, such as less than 0.2 mole %, or less than 0.1 mole %.

The hydrogenated tail gas is added directly to the ATR, CPO or POx, as illustrated in the enclosed Figures. The term "directly" means without any intermediate processes which change the chemical composition of the hydrogenated tail gas, e.g. without a steam reformer between said hydrogenation stage and said ATR, CPO or POx.

In a broader aspect the invention encompasses also a method for reducing metal dusting in an apparatus, said apparatus containing an off-gas, said method comprising the removal of olefins from said off-gas. In particular, olefins are removed by hydrogenation thereof. The method is particularly useful for the reduction of metal dusting in ATR, CPO or POx and other downstream equipment through which off-gas is passed. The invention encompasses a method for the reduction of metal dusting in an ATR, CPO or POx and further downstream equipment by removing the content of olefins in an off-gas to be passed through the ATR, CPO or POx.

Preferably, said step of removing the content of olefins is a hydrogenation stage.

As used herein the term "further downstream equipment" means waste heat boiler and/or steam superheater located downstream the ATR, CPO or POx and which are used for cooling the synthesis gas under the production of steam.

As used herein the term "removing the content of olefins" means reducing the content of olefins in the gas to less than 0.2 mole %, preferably less than 0.1 mole %.

As used herein the term "off-gas" means any gas containing hydrocarbons and olefins, which has to be reformed in the ATR, CPO or POx to form a synthesis gas comprising hydrogen and carbon monoxide. The off-gas is preferably tail gas from Fischer-Tropsch synthesis or tail gas from downstream process for production of gasoline, such as a process in which gasoline is produced from oxygenates comprising methanol and dimethyl ether, for instance via the so-called TIGAS process as disclosed in U.S. Pat. Nos. 4,520,216 and 4,481,305.

The invention encompasses also the use of a gas free of olefins as means for the reduction of metal dusting of the metal parts of apparatus in direct contact with the gas. Preferably the apparatus in direct contact with the gas is an ATR, CPO or POx. Preferably, the gas is an off-gas; i.e. the waste gas from an industrial process such as gasoline synthesis as defined above.

As used herein and in accordance above the term "gas free of olefins" a gas with less than 0.2 mole %, preferably less than 0.1 mole % olefins.

As used herein the term "in direct contact with the gas" means that the gas free of olefins is added directly to the equipment or to a separate hydrocarbon feedstock without first being passed through an intermediate stage of reforming, such as steam reforming.

Features of the Invention:

The invention is also disclosed by the below features in correspondence with the appended claims.

1. Process for the production of synthesis gas from a hydrocarbon feedstock with reduced metal dusting potential in at least the burner parts of an autothermal reformer (ATR), catalytic partial oxidation reactor (CPO), or partial oxidation reactor (POx) comprising: passing said hydrocarbon feedstock through an ATR, CPO or POx, and withdrawing a stream of hot effluent synthesis gas from the ATR, CPO or POx, passing tail gas from a Fischer-Tropsch synthesis stage through a hydrogenation stage to produce a hydrogenated tail gas and adding the hydrogenated tail gas directly to said ATR, CPO or POx.
2. Process according to feature 1 wherein said hydrocarbon feedstock is a gas that has passed through at least one adiabatic pre-reforming stage.
3. Process according to feature 1 or 2 wherein said hydrocarbon feedstock is a gas that has passed through at least one steam reforming stage.
4. Process according to any of features 1 to 3 wherein said hydrocarbon feedstock is a gas mixture resulting from dividing a raw hydrocarbon feed gas into two streams, passing the first stream through at least one steam reforming stage to form a primary reformed gas, using the second stream as a by-pass stream to said steam reforming stage, and subsequently combining said primary reformed gas with the by-pass stream to form said hydrocarbon feedstock.
5. Process according to any of features 1 to 3 comprising dividing a raw hydrocarbon feed gas into two streams, by which one of the streams becomes said hydrocarbon feedstock, and passing the other stream through at least one steam reforming stage to form a reformed gas.
6. Process according to any of features 3-5 wherein the steam reforming stage is heat exchange reforming, and where at least a portion of the hot effluent synthesis gas from the ATR, CPO, or POx is used as heating medium in said heat exchange reforming.
7. Process according to feature 5 or 6 wherein said hot effluent synthesis gas is combined with said reformed gas before, during or after said hot effluent synthesis gas has delivered heat to the heat exchange reforming.
8. Process according to feature 6 or 7 comprising adding a stream comprising steam to said hot effluent synthesis gas, said reformed gas, or the combined stream of hot effluent synthesis gas and reformed gas.
9. Process according to any of features 4 to 8 wherein the at least one adiabatic pre-reforming stage is conducted prior to dividing said raw hydrocarbon feed.
10. Process according to any of features 1 to 9 comprising mixing the hydrogenated tail gas with the hydrocarbon feedstock prior to conducting reforming in the ATR, CPO or POx.
11. Process according to any of features 1-9 comprising adding the hydrogenated tail gas to the ATR, CPO or POx as a separate stream.
12. Process according to any of features 4, 8 and 9 comprising mixing the hydrogenated tail gas with said by-pass stream prior to conducting reforming in the ATR, CPO or POx.
13. Process according to any of features 4, 6, 8 and 9 comprising mixing the hydrogenated tail gas with said primary reformed gas.
14. Process according to any of features 1-13 further comprising converting the synthesis gas into liquid hydrocarbons via Fischer-Tropsch synthesis.
15. A method for reducing metal dusting in an apparatus, said apparatus containing an off-gas, said method comprising the removal of olefins from said off-gas.
16. The method according to feature 15, wherein olefins are removed by hydrogenation thereof.
17. The method according to any one of features 15-16 wherein the apparatus is an ATR, CPO or POx
18. The use of a gas free of olefins for the reduction of metal dusting of the metal parts of apparatus in direct contact with said gas.
19. The use according to feature 18, wherein the apparatus in direct contact with the gas is an ATR, CPO or POx.
20. The use according to any one of features 18-19, wherein the gas is a tail gas from a Fischer Tropsch synthesis.
21. The use according to any one of features 18-20, wherein the gas free of olefins is obtained by hydrogenation of said olefins to alkanes.

BRIEF DESCRIPTION OF THE DRAWINGS

The invention is further illustrated by reference to the accompanying figures.

DETAILED DESCRIPTION OF FIGURES

Figure 1:
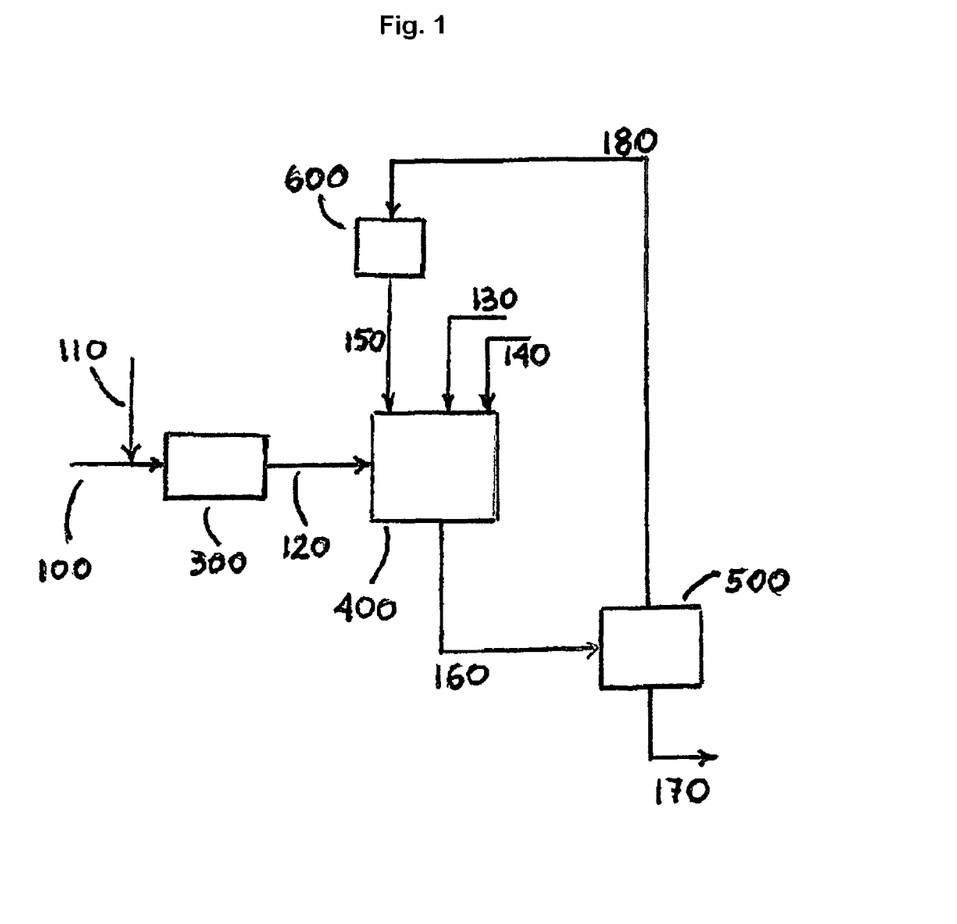
FIG. 1 shows a schematic view of the invention when using a stand-alone autothermal reformer yet including a pre-reformer.

The accompanying FIG. 1 shows a general schematic view of an embodiment for the production of synthesis gas for Fischer-Tropsch synthesis using a stand-alone autothermal reformer. Clean (free of sulphur and other poisons to reforming catalysts) hydrocarbon feed gas 100 such as natural gas or other hydrocarbon containing gas source is mixed with process steam 110, optionally partly via saturator/humidifier. The mixture is preheated and pre-reformed adiabatically in pre-reformer 300 in order to convert any higher hydrocarbons into $H_2$, $CO$, $CO_2$ and $CH_4$. This resulting hydrocarbon feedstock mixture 120 is fed to the autothermal reformer 400 together with oxygen 130, protection steam 140 and hydrogenated tail gas 150. From the autothermal reformer 400 at hot effluent of synthesis gas 160 is withdrawn and further processed to form the synthesis gas feed to the downstream Fischer-Tropsch section 500. Liquid hydrocarbons 170 are produced and tail gas recycle stream 180 is passed through hydrogenating stage 600 prior to entering the autothermal reformer 400. Notably, hydrogenated tail gas is added directly from the hydrogenator to the autothermal reformer 400.

Figure 2:
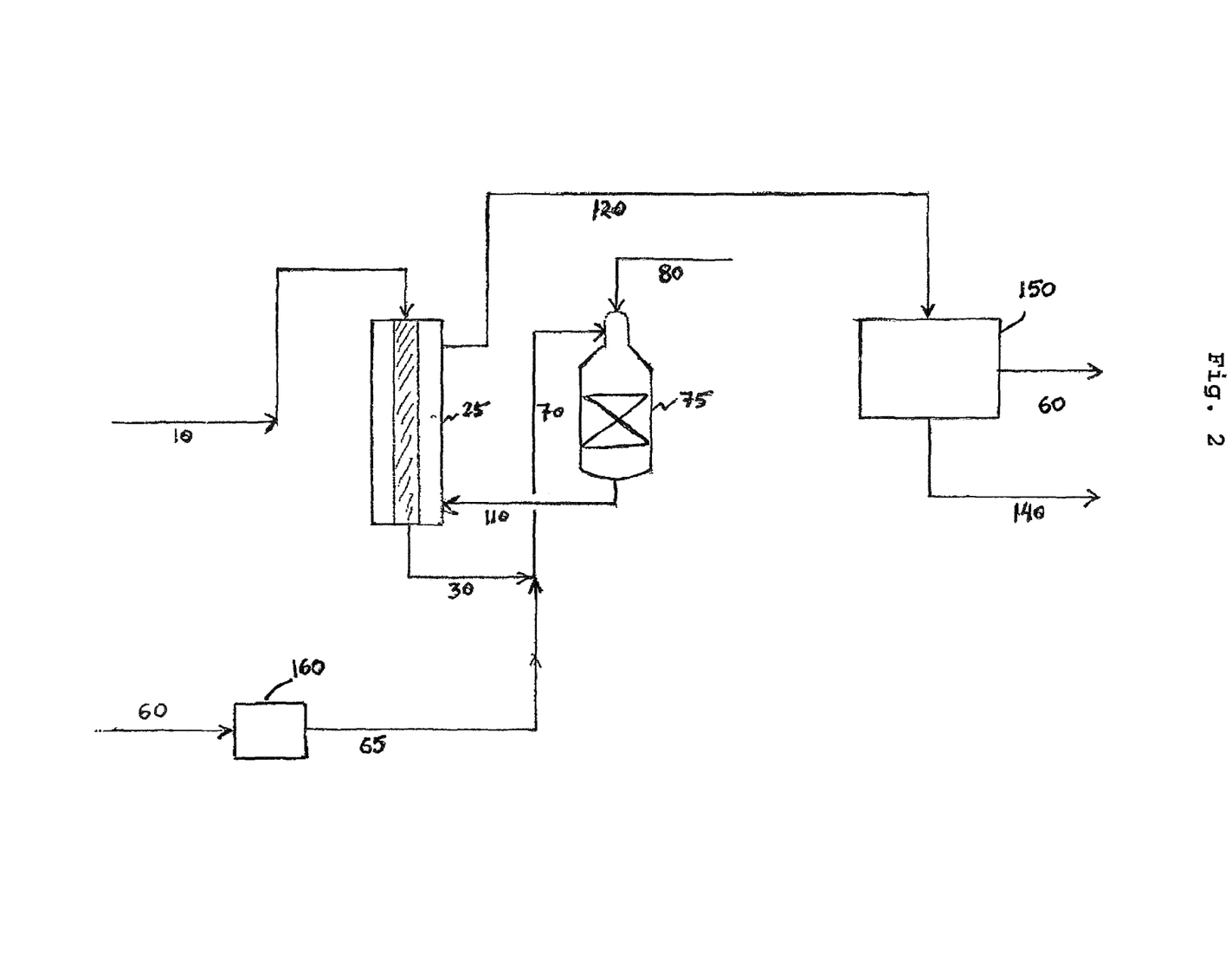
FIG. 2 shows heat exchange reforming and autothermal reforming in series with hydrogenated tail gas addition to the primary reformed gas.

In FIG. 2, a mixture of the raw hydrocarbon feed gas and steam 10 is passed to heat-exchange reformer 25 where it is catalytically steam reformed and thereafter leaves the heat-exchange reformer as stream 30. The primary reformed gas stream 30 is mixed with hydrogenated tail gas 65 from Fischer-Tropsch section 150 forming the ATR feed stream 70. The mixed stream 70 is fed to an autothermal reformer 75 with oxidant 80 and protection steam (not shown) also being supplied. The primary reformed gas is partially combusted and brought towards equilibrium over reforming catalyst in the autothermal reformer 75. The hot effluent synthesis gas 110 from the autothermal reformer is passed through the heat exchange reformer 25. The synthesis gas is cooled by heat exchange with the gas undergoing reforming over the catalyst in the heat-exchange reformer 25. The thus cooled synthesis gas leaves the heat exchange reformer as stream 120 and is further processed to form the synthesis gas feed to the Fischer-Tropsch section 150 downstream. Liquid hydrocarbon products 140 are withdrawn together with a tail gas recycle stream 60. The tail gas recycle stream 60 passes through hydrogenator 160 to form hydrogenated tail gas stream 65 before being combined with primary reformed gas 30. Notably, hydrogenated tail gas is added directly from the hydrogenator to the autothermal reformer 400.

Figure 3:
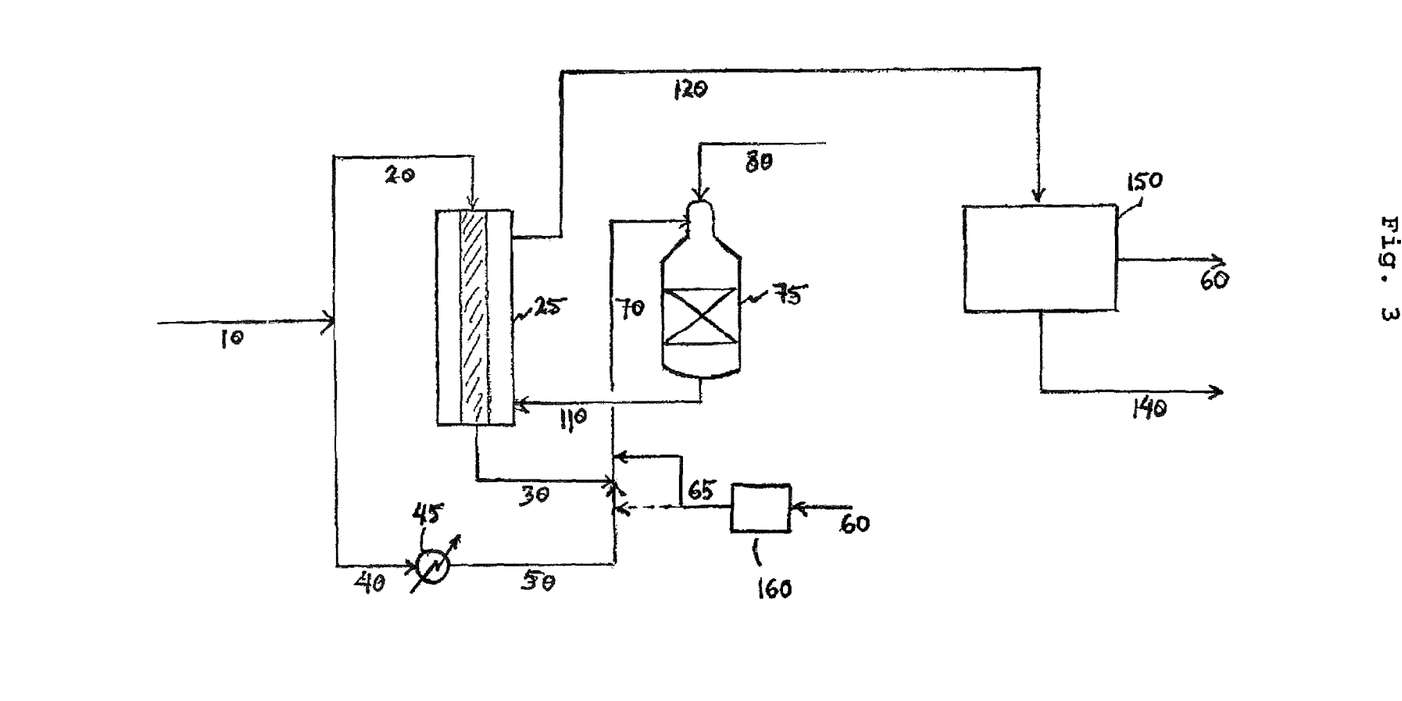
FIG. 3 shows a process with by-pass of the primary reforming stage, with addition of hydrogenated tail gas to the by-pass stream, or to the combined stream of primary reformed gas and by-pass stream.

In FIG. 3, a mixture of raw hydrocarbon feed gas (10) is divided into two streams 20 and 40. The first stream 20 is fed to the heat-exchange reformer 25 where it is catalytically steam reformed and thereafter leaves the heat-exchange reformer as primary reformed gas 30. The second stream 40 is preheated in a heat exchanger 45 and bypasses the heat exchange reformer. The primary reformed gas 30 is mixed with the preheated second stream 50. Hydrogenated tail gas 65 is added to this mixed stream or to the preheated second stream 50 thus forming the ATR feed stream 70. The ATR feed stream is fed to the autothermal reformer 75 to which oxidant 80 and protection steam (not shown) are also supplied. The ATR feed stream is partially combusted and brought towards equilibrium over reforming catalyst in the autothermal reformer 75. The hot effluent synthesis gas 110 is passed through the heat exchange reformer 25. The mixture stream is cooled by heat exchange with the gas undergoing reforming over the catalyst in the heat-exchange reformer 25. The thus cooled synthesis gas leaves the heat exchange reformer as stream 120 and is further processed to form the synthesis gas feed to the Fischer-Tropsch section 150 downstream. Liquid hydrocarbon products 140 are withdrawn together with a tail gas recycle stream 60. The tail gas recycle stream 60 passes through hydrogenator 160 to form hydrogenated tail gas stream 65 which is then combined with primary reformed gas 30 or by-pass stream 50. Alternatively, the hydrogenated tail gas 65 may also be added to the primary reformed stream 30. Notably, hydrogenated tail gas is added directly from the hydrogenator to the autothermal reformer 400.

EXAMPLE

Two tests were made in the same experimental setup: An 800 mm long sample of Inconel 690 was placed in a reactor. The reactor was placed in an oven with three heating zones. The temperature of the Inconel 690 sample varied with the position in the oven. The sample temperatures were 200 to 640° C. The sample was exposed to a continuous flow of gas with the composition given in Table 1 as Test 1. The flow rate was 100 Nl/h. The pressure was 29 barg. The conditions were kept for 626 hours. The sample was examined after the test using stereo microscope and scanning electron microscope. The sample was attacked by metal dusting corrosion.

The second test was made analogous to the first test, with the exceptions that the gas composition used was as given in Table 1 as Test 2 and the conditions were kept for 672 hours. Examination of the sample after the test showed that the sample was not attacked by metal dusting corrosion.

TABLE 1

| Gas compositions (mole %) | | |
| --- | --- | --- |
| Component | Test 1 | Test 2 |
| Hydrogen | 12.1 | 12.1 |
| Water | 22.6 | 22.6 |
| Carbon monoxide | 6.9 | 6.9 |
| Carbon dioxide | 7.8 | 7.8 |
| Ethylene | 0.14 | 0 |
| Ethane | 0 | 0.14 |
| Methane | 49.8 | 49.8 |
| Propane | 0.45 | 0.45 |
| 1-Butene | 0.21 | 0 |
| Butane | 0 | 0.21 |

The two gas compositions in the two tests are identical with the exception that the gas in test 1 contains the olefins (alkenes), whereas the gas in test 2 contains the corresponding alkanes. Metal dusting attack occurs in Test 1 but not in Test 2, which is of longer duration.

The presence of alkenes makes a gas more aggressive with respect to metal dusting corrosion. Thus, the use of a hydrogenated tail gas conveys the reduction or elimination of metal dusting compared to a situation where tail gas is used without being hydrogenated.

The invention claimed is:

1. A process for the production of synthesis gas from a hydrocarbon feedstock with reduced metal dusting in at least burner parts of an autothermal reformer (ATR), catalytic partial oxidation reactor (CPO), or partial oxidation reactor (POx), the process comprising the steps of:
   passing said hydrocarbon feedstock through an ATR, CPO, or POx; and withdrawing a stream of hot effluent synthesis gas from the ATR, CPO or POx;
   passing tail gas from a Fischer-Tropsch synthesis gas stage through a hydrogenation stage comprising a copper hydrogenation catalyst to produce a hydrogenated tail gas; and
   adding the hydrogenated tail gas directly to said ATR, CPO or POx.

2. The process according to claim 1 wherein said hydrocarbon feedstock is a gas that has passed through at least one adiabatic pre-reforming stage.

3. The process according to claim 1 wherein said hydrocarbon feedstock is a gas that has passed through at least one steam reforming stage.

4. The process according to claim 1 wherein said hydrocarbon feedstock is a gas mixture resulting from dividing a raw hydrocarbon feed gas into two streams, passing the first stream through at least one steam reforming stage to form a primary reformed gas, using the second stream as a by-pass stream to said steam reforming stage, and subsequently combining said primary reformed gas with the by-pass stream to form said hydrocarbon feedstock.

5. The process according to claim 1 comprising dividing a raw hydrocarbon feed gas into two streams, by which one of the streams becomes said hydrocarbon feedstock, and passing the other stream through at least one steam reforming stage to form a reformed gas.

6. The process according to claim 3 wherein the steam reforming stage is heat exchange reforming, and where at least a portion of the hot effluent synthesis gas from the ATR, CPO, or POx is used as heating medium in said heat exchange reforming.

7. The process according to claim 6 wherein said hot effluent synthesis gas is combined with said reformed gas before, during or after said hot effluent synthesis gas has delivered heat to the heat exchange reforming.

8. The process according to claim 7 comprising adding a stream comprising steam to said hot effluent synthesis gas, to said reformed gas, or to the combined stream of hot effluent synthesis gas and reformed gas.

9. The process according to claim 4 wherein at least one adiabatic pre-reforming stage is conducted prior to dividing said raw hydrocarbon feed.

10. The process according to claim 1 comprising mixing the hydrogenated tail gas with the hydrocarbon feedstock prior to conducting reforming in the ATR, CPO or POx.

11. The process according to claim 1 comprising adding the hydrogenated tail gas to the ATR, CPO or POx as a separate stream.

12. The process according to claim 4 comprising mixing the hydrogenated tail gas with said by-pass stream prior to conducting reforming in the ATR, CPO or POx.

13. The process according to claim 4 comprising mixing the hydrogenated tail gas with said primary reformed gas.

14. Process The process according to claim 1 further comprising converting the synthesis gas into liquid hydrocarbons via Fischer-Tropsch synthesis.

* * * * *